(12) United States Patent
Janke et al.

(10) Patent No.: US 6,240,321 B1
(45) Date of Patent: May 29, 2001

(54) EXPANDABLE SEAL FOR USE WITH MEDICAL DEVICE AND SYSTEM

(75) Inventors: Aaron W. Janke, St. Paul; Larry L. Hum, Cottage Grove; Randy Westlund, Minneapolis; Ronald W. Heil, Jr., Roseville; Bruce Tockman, Scandia, all of MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 09/133,310

(22) Filed: Aug. 12, 1998

(51) Int. Cl.[7] .................................................. A61N 1/05
(52) U.S. Cl. ........................ 607/122; 607/116; 600/374
(58) Field of Search ................................. 607/120, 116, 607/119, 122, 126, 127, 153, 9; 600/375, 374, 373

(56) References Cited

U.S. PATENT DOCUMENTS

| | | | |
|---|---|---|---|
| 4,311,153 | 1/1982 | Smits | 128/785 |
| 4,506,680 | 3/1985 | Stokes | 128/786 |
| 4,577,642 * | 3/1986 | Stokes | 607/120 |
| 4,649,938 | 3/1987 | McArthur | 128/785 |
| 4,819,661 | 4/1989 | Heil, Jr. et al. | 128/786 |
| 4,886,074 | 12/1989 | Bisping | 128/785 |
| 4,953,564 * | 9/1990 | Berthelsen | 607/120 |
| 5,002,067 * | 3/1991 | Berthelsen et al. | 607/120 |
| 5,003,992 * | 4/1991 | Holleman et al. | 607/120 |
| 5,015,238 | 5/1991 | Solomon et al. | 604/164 |
| 5,397,343 * | 3/1995 | Smits | 607/120 |
| 5,425,755 | 6/1995 | Doan | 607/119 |
| 5,447,534 | 9/1995 | Jammet | 607/127 |
| 5,476,501 | 12/1995 | Stewart et al. | 607/127 |
| 5,476,708 | 10/1995 | Doan et al. | 607/127 |
| 5,496,360 * | 3/1996 | Hoffmann et al. | 607/120 |
| 5,507,724 | 4/1996 | Hofmann et al. | 604/53 |
| 5,522,874 | 6/1996 | Gates | 607/127 |
| 5,531,780 | 7/1996 | Vachon | 607/120 |
| 5,693,034 | 12/1997 | Buscemi et al. | 604/265 |
| 5,755,766 | 5/1998 | Chastain et al. | 607/122 |

FOREIGN PATENT DOCUMENTS 0057877   8/1982   (EP) .................................... 607/121

OTHER PUBLICATIONS

DiColo, G., et al., "Effect of Water–Soluble Additives on Drug Release From Silicone Rubber Matrices", *Int. J. Pharm.*, vol. 30, 1–7, (May 1986).

Fedors, R.F., "Osmotic Effects in Water Absorption by Polymers", *Polymer*, vol. 21, 207–212, (Feb. 1980).

Golomb, G., et al., "The Relationship Between Drug Release Rate, Particle Size and Swelling of Silicone Matrices", *Journal of Controlled Release*, vol. 12, 121–132, (1990).

* cited by examiner

*Primary Examiner*—Kennedy Schaetzle
(74) *Attorney, Agent, or Firm*—Schwegman, Lundberg, Woessner & Kluth, P.A.

(57) ABSTRACT

A seal adapted for use with medical devices is provided with a lead having a distal tip electrode. The distal tip of the lead is adapted for implantation on or about the heart and for connection to a system for monitoring or stimulating cardiac activity. The lead can include a fixation helix for securing the electrode to cardiac tissue. The lead assembly can alternatively include an open lumen lead tip. A seal is provided within the lead tip assembly such that the seal is expanded to prevent or limit further entry of fluids through the lead tip. The seal includes an expandable matrix, such as a hydrogel. The seal is formed on or within the lead when the lead and the seal comes into contact with a fluid and expands. The seal is also formed as a plug which is deployed through the medical device, and expands as the plug absorbs fluid. A housing incorporating the seal can also be attached to a portion of the medical device to provide the seal.

37 Claims, 11 Drawing Sheets

EXPANDABLE SEAL FOR USE WITH MEDICAL DEVICE AND SYSTEM

FIELD OF THE INVENTION

The present invention relates generally to medical devices, such as leads and catheters. More particularly, it pertains to expandable seals for medical devices such as leads and catheters.

BACKGROUND OF THE INVENTION

Leads implanted in or about the heart have been used to reverse (i.e., defibrillate or cardiovert) certain life threatening arrhythmias, or to stimulate contraction (pacing) of the heart. Electrical energy is applied to the heart via the leads to return the heart to normal rhythm. Leads have also been used to sense in the atrium or ventricle of the heart and to deliver pacing pulses to the atrium or ventricle. The same lead used to sense the condition is sometimes also used in the process of delivering a corrective pulse or signal from the pulse generator of the pacemaker.

Cardiac pacing may be performed by the transvenous method or by leads implanted directly onto the ventricular epicardium. Most commonly, permanent transvenous pacing is performed using a lead positioned within one or more chambers of the heart. A lead, sometimes referred to as a catheter, may be positioned in the right ventricle or in the right atrium through a subclavian vein, and the lead terminal pins are attached to a pacemaker which is implanted subcutaneously. The lead may also be positioned in both chambers, depending on the lead, as when a lead passes through the atrium to the ventricle. Sense electrodes may be positioned within the atrium or the ventricle of the heart.

Pacemaker leads represent the electrical link between the pulse generator and the heart tissue which is to be excited. These pacemaker leads include single or multiconductor coils of insulated wire having an insulating sheath. The coils provide a cylindrical envelope, many times referred to as a lumen, which provides a space into which a stiffening stylet can be inserted. The conductive coil is connected to an electrode in an electrode assembly at a distal end of a pacing lead.

After the electrode assembly is positioned at a desired location within the heart, it is desirable to provide some method for securing the electrode assembly at that location. One approach is to use a passive device which has structure to allow for tissue growth surrounding the structure to affix the electrode assembly to the heart. Another approach is to use an active device where mechanical fixation devices are used to firmly anchor the electrodes in the heart. One type of mechanical fixation device used is a corkscrew, or a helix. During placement of the lead, the tip of the lead travels intravenously through veins and the heart. While traveling through the veins, the helix at the tip of the lead may snag or attach to the side wall of the vein. Since this is highly undesirable as it may cause damage or other complications to a patient, retractable helixes have been provided for leads.

The practitioner must maintain the electrode pressed against the wall of the cavity before shifting the screw. When the screw is shifted, the electrode may be correctly in contact with the wall, and the fixation screw, as it travels out of the body of the electrode, penetrates and becomes hooked in the tissue of the wall. Alternatively, the electrode may stop short of the wall of the cavity and it may be necessary for the practitioner to start again by retracting the screw and then turning the helix out again into the cardiac tissue. Thus, it is important for the helix to rotate freely within the electrode.

During use, the lead provides and receives critical information to and from the heart. The lead, therefore, must remain in sufficient operative condition without interference from entry of bodily fluids. To prevent entry of bodily fluids into the lead, a seal can be provided at the distal end of the lead. Conventional leads often use O-rings or puncture seals to seal the distal end of the lead from entry of bodily fluids. The O-ring seals can be difficult to manufacture due to dimensional constraints which also affects the extension/retraction mechanism of the lead, as well as the effectiveness of the seal. Puncture seals also may increase the difficultly of using the helix, since the helix needs to puncture the seal and the puncture seals can increase the friction between the extension mechanism and the seal. The friction makes it more difficult to extend or retract the extension mechanism and the helix. In addition, the structural integrity of the puncture seal can be jeopardized if the seal continues to tear from repeated movement and/or stress from the fixation screw.

Accordingly, there is a need for a lead which is sufficiently sealed from the environment. What is further needed is a seal which does not interfere with the extension and retraction of the helix.

SUMMARY OF THE INVENTION

A body-implantable lead assembly is provided comprising a lead, one end being adapted to be connected to an electrical supply for providing or receiving electrical pulses. The lead further comprises a distal tip which is adapted to be connected to tissue of a living body. The lead also has a sheath of material inert to body materials and fluids and at least one conductor extending through the lead body.

The distal tip electrode is adapted for implantation proximate to or within the heart while connected with a system for monitoring or stimulating cardiac activity. In another embodiment, the distal tip electrode assembly is adapted for implantation proximate to the heart while connected with a system for monitoring or stimulating cardiac activity. The distal tip electrode includes, in one embodiment, an electrode tip, a mesh screen disposed at a distal end of the electrode tip, a fixation helix disposed within the electrode tip, and a hydrogel seal. The helix is retractable, and is in contact with a movement mechanism. The movement mechanism provides for retracting the helix, such as during travel of the electrode tip through veins. In another embodiment, the electrode tip further includes a piston for moving the helix. The piston can further include a slot for receiving a stylet. When engaged and rotated, the piston provides movement to the helix. The piston is coated with the hydrogel seal, in one embodiment, which is adapted to expand upon contact with bodily fluid.

In another configuration, a distal tip electrode is provided which is adapted for implantation proximate to the heart, while optionally connected with a system for monitoring or stimulating cardiac activity. The distal tip electrode includes a seal comprised of an expandable matrix which is adapted to expand upon contact with fluid. The seal can be in the form of a plug which is inserted into the electrode, or a medical device, using an advancing tool. The plug can be molded of the expandable material into a variety of shapes, for instance a ring, or including a tapered surface. The ring shape can also be used for surrounding an internal lead structure disposed within the lead. The plug can optionally include features which frictionally engage an encompassing surface and prevent premature removal of the advancing tool. In another embodiment, the seal is in the form of an end cap which is affixed to the distal tip of the electrode. Alternatively, the expandable matrix is disposed on the interior of a housing which is secured to the electrode.

The provided medical device, which includes an electrode tip, supplies an extension/retraction mechanism which is sealed from exposure to fluids. The lead avoids deterioration of its function by entry of liquid inside the lead, owing to the provision of a highly effective seal which does not interfere with the helix. In addition, the seal remains functional when the lead is removed for short periods of time from an environment filled or partially filled with fluid. Yet another advantage is that the lead and the seal permit rotating the extension/retraction mechanism until it penetrates the cardiac tissue without limitation on the number of rotations until proper anchorage has been achieved, and without significant friction imparted to the extension/retraction mechanism.

These and other embodiments, aspects, advantages, and features of the present invention will be set forth in part in the description which follows, and in part will become apparent to those skilled in the art by reference to the following description of the invention and referenced drawings or by practice of the invention. The aspects, advantages, and features of the invention are realized and attained by means of the instrumentalities, procedures, and combinations particularly pointed out in the appended claims and their equivalents.

DESCRIPTION OF THE EMBODIMENTS

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the spirit and scope of the present invention. Therefore, the following detailed description is not to be taken in a limiting sense, and the scope of the present invention is defined by the appended claims and their equivalents.

Figure 1:
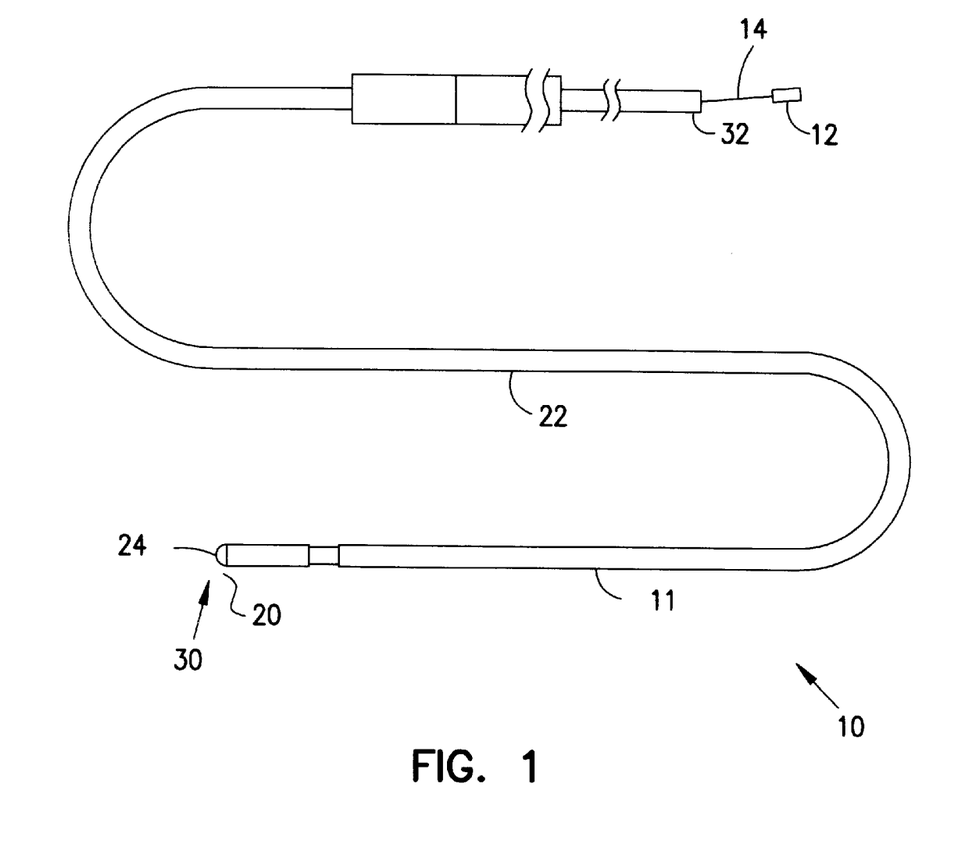
FIG. 1 is a side elevational view illustrating a lead constructed in accordance with one embodiment of the present invention.
Figure 2A:
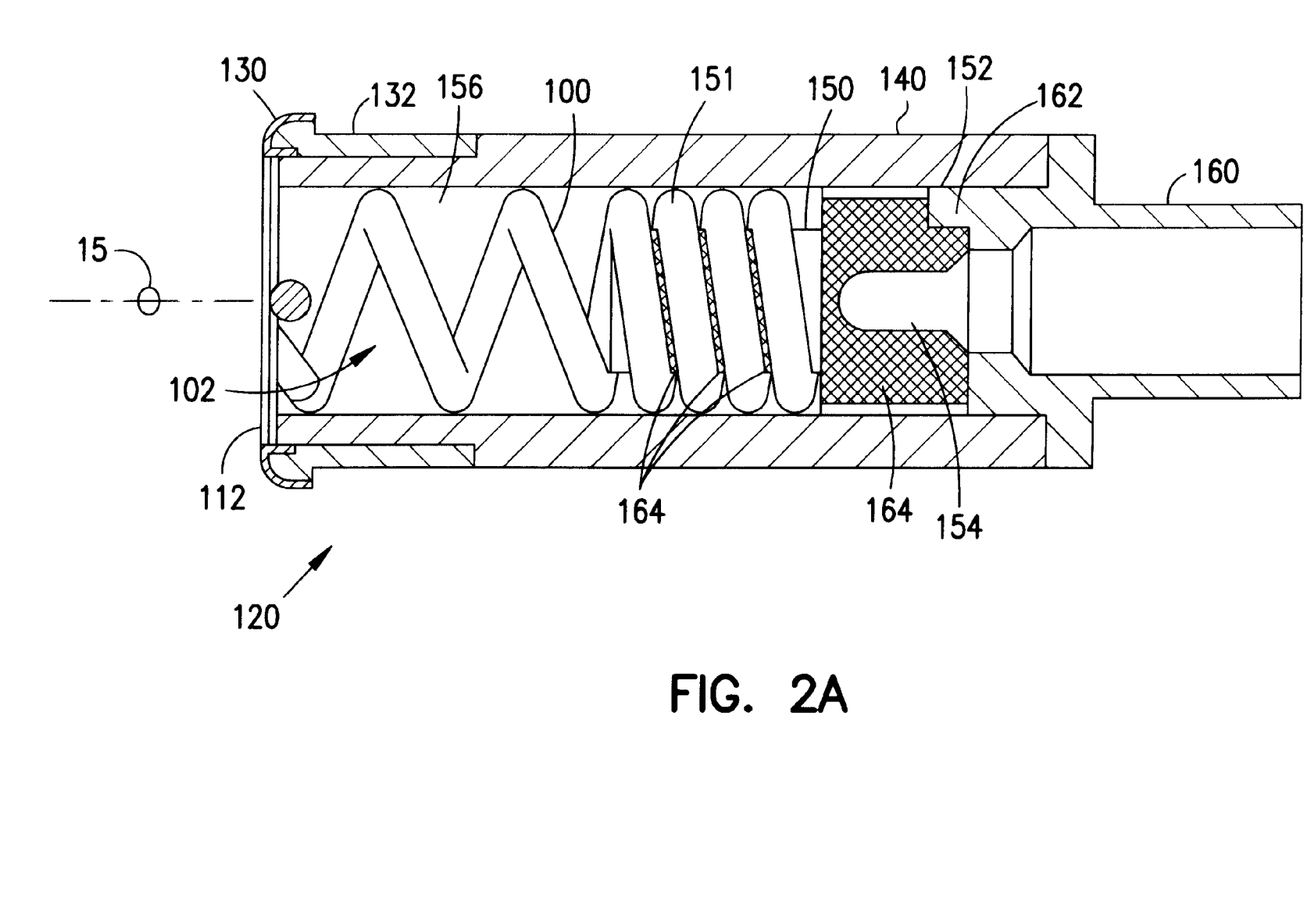
FIG. 2A is a cross-sectional view of an electrode tip of a lead for monitoring and stimulating the heart constructed in accordance with one embodiment of the present invention.
Figure 2B:
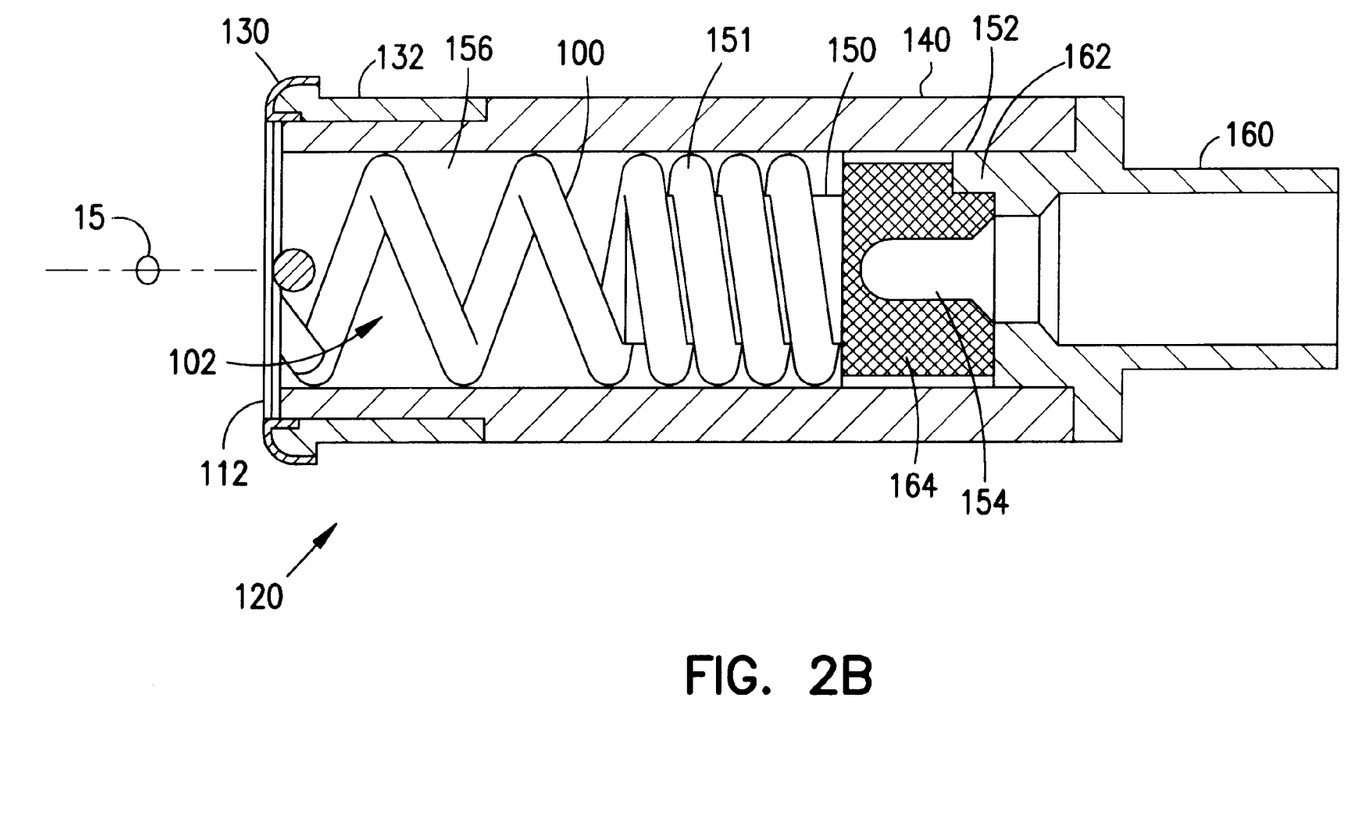
FIG. 2B is a cross-sectional view of an electrode tip of a lead for monitoring and stimulating the heart constructed in accordance with one embodiment.
Figure 2C:
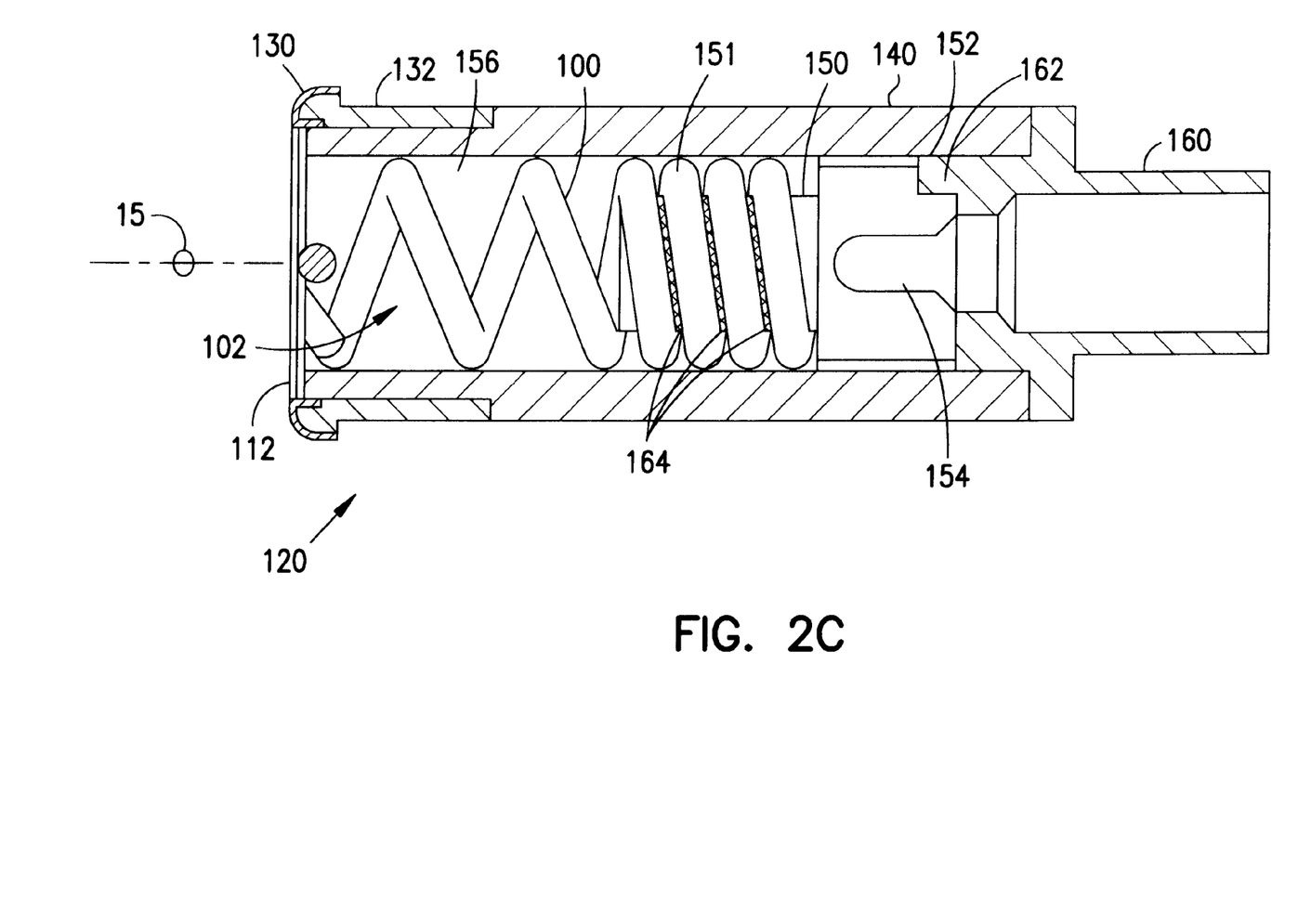
FIG. 2C is a cross-sectional view of an electrode tip of a lead for monitoring and stimulating the heart constructed in accordance with one embodiment.
Figure 3A:
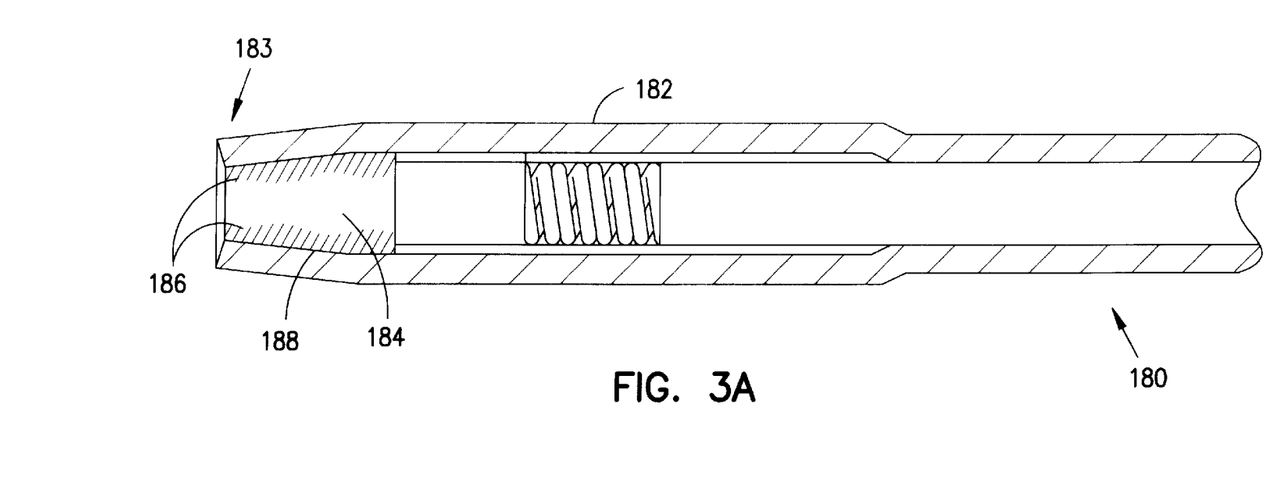
FIG. 3A is a cross-sectional view of an electrode tip of a lead for monitoring and stimulating the heart constructed in accordance with one embodiment of the present invention.
Figure 3B:
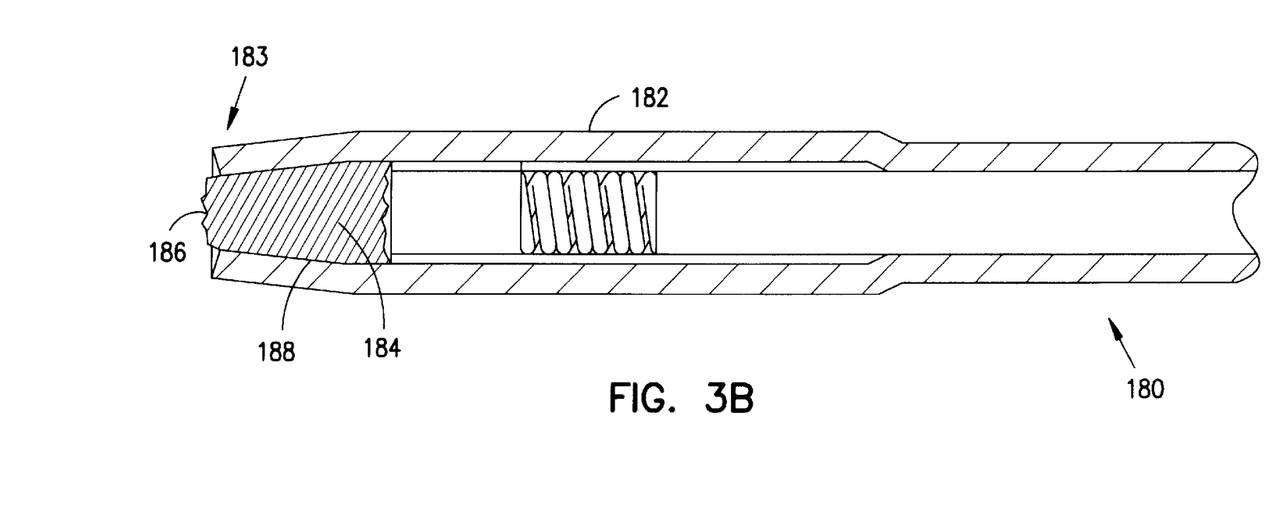
FIG. 3B is a cross-sectional view of an electrode tip of a lead for monitoring and stimulating the heart constructed in accordance with one embodiment of the present invention.

One embodiment of a lead 10 is illustrated in FIG. 1. The lead 10, in one embodiment, comprises a lead body 11, and extends from a proximal end 32 to a distal end 30. An elongate conductor is contained within the lead body 11, and a lead tip 20 is disposed proximate the distal end 30. In one embodiment, an electrode tip assembly 24 is contained in the lead tip 20 (FIG. 2). In another embodiment, the lead tip 20 comprises an open lumen lead tip (FIGS. 3A and 3B). In addition, a stylet 14 is shown, which in one embodiment is inserted into the lead body 11.

A helix 100 (FIG. 2) comprises an electrical conductor coil, is contained in the retractable lead tip assembly 24, in another embodiment. The helix 100 extends and retracts by rotation of the stylet 14, as will be discussed further below. Although a brady lead body is shown, other medical devices or other leads, such as tachy leads could also be used. In one embodiment, the lead body 11 is at least partially covered by a biocompatible insulating material 22. Silicone rubber or other insulating material can be used for covering the lead body 11.

In one embodiment, the helix 100 is formed of electrically conductive material offering low electrical resistance and which is also resistant to corrosion by body fluids. In another embodiment, the helix 100 may be coated with an insulative material. A platinum-iridium alloy is an example of a suitable conductive material. Another example is a conductive helix partially coated with Parylene. The Parylene insulative coating effectively increases in vitro "pacing impedance". Application of Parylene to the metallic fixation helix produces the desired increase in impedance compared to an uninsulated helix as well as other existing designs. Alternatively, in another configuration, the helix 100 is electrically inactive. The helix 100 can be made electrically active or inactive to change sensing and pacing characteristics as needed.

Referring to FIGS. 2A, 2B, and 2C the helix 100 of the lead 10, in one embodiment, defines a lumen 102 therethrough and thereby is adapted to receive a stiffening stylet 14 that extends through the length of the lead 10. The lumen 102, however, can also be defined by other portions of the electrode tip assembly 24. The stylet 14 (FIG. 1) stiffens the lead 10, and can be manipulated to introduce an appropriate curvature to the lead 10, facilitating the insertion of the lead 10 into and through a vein and through an intracardiac valve to advance the distal end 30 of the lead 10 into the heart, for example into the right ventricle of the heart. A stylet knob 12 (FIG. 1) is coupled with the stylet 14 for rotating the stylet 14 and advancing the helix 100 into tissue of the heart.

In another embodiment, the lead 10 has an electrode tip 120 which is provided with a mesh screen 130. The mesh screen 130 covers at least a portion of an end surface 112 of the lead 10, and serves as the pacing/sensing interface with cardiac tissue. If the helix 100 is electrically active, it too can help serve as a pacing or sensing interface. The mesh screen 130 is of a porous construction, made of electrically conductive, corrosion resistant material. Using a mesh screen 130, for example having a porous construction, advantageously allows for fibrotic ingrowth. This provides for a further anchoring of the electrode tip 120 and also increases the sensing capability of the lead 110 by increasing the surface area in contact with the cardiac tissue. The impedance of the mesh screen can be also controlled by providing a partially insulating mesh screen. The mesh screen 130, in one embodiment, is attached to an electrode collar 132, which can be electrically active.

Disposed within the lead 10, in one embodiment, is a lead fastener for securing the lead 10 to cardiac tissue. The lead fastener can be disposed along the radial axis 15 (FIGS. 2A, 2B and 2C) of the electrode lead 10. In one embodiment, the lead fastener comprises a fixation helix 100. The fixation helix 100 can be made electrically active or inactive as discussed above. Using a conductor coil such as helix 100 has been shown to be capable of withstanding constant, rapidly repeated flexing over a period of time which can be measured in years. The helix 100 is wound relatively tightly, with a slight space between adjacent turns. This closely coiled construction provides a maximum number of conductor turns per unit length, thereby providing optimum strain distribution. The spirally coiled spring construction of helix 100 also permits a substantial degree of elongation, within the elastic limits of the material, as well as distribution along the conductor of flexing stresses which otherwise might be concentrated at a particular point.

Attached to the fixation helix 100, in one embodiment, is a piston 150. The piston 150 has a stylet slot 154 which is configured to mate with the bladed locking stylet 14 at the stylet slot 154. The stylet slot 154 acts as an interface between the stylet 14 and the helix 100. The stylet 14, coupled the piston 150 at the stylet slot 154, extends and retracts the fixation helix 100 when the stylet 14 is rotated. The piston 150 can either be electrically active or inactive. The piston 150, in another embodiment, also has a base slot 152, which allows the piston 150 to mate with a base 160. The helix 100 with or without the piston form a movement mechanism which facilitates the implantation of the lead 10 into a heart.

Fitted with a knob 162, as shown in FIGS. 2A, 2B and 2C the base 160, in one embodiment, mates with the base slot 152 of the piston 150. The base 160 serves as a stop once the fixation helix 100 is fully retracted. The base 160, which can be electrically conductive, is adapted to allow passage of a bladed locking stylet 14 and attachment of electrode coils.

A housing 140, which is electrically conductive in one embodiment, encapsulates the piston 150 and the fixation helix 100. In one embodiment, the housing 140 is disposed about the piston 150, creating an annular gap 156 therebetween. Insulation (not shown) is disposed about the housing 140 and collar 132. A suitable material for the insulation is, for example, silicone rubber, or other materials which are inert and well tolerated by body tissue are also appropriate. The housing 140 is coupled with the electrode collar 132 and transmits electrical signals from the electrode collar 132 to the base 160.

In another embodiment, the electrode tip 120 has a hydrogel seal 164 disposed therein as shown in FIGS. 2A, 2B, and 2C. In one embodiment, the piston 150 is coated with the hydrogel seal 164. In another embodiment, a portion of the helix 100 is coated with the hydrogel seal 164. In a further embodiment, both the piston 150 and the helix 100 may be coated with a hydrogel 164. For example, a tight-wound portion 151 of the helix 100 is coated with the hydrogel seal 164. The hydrogel seal 164 is adapted to expand upon contact with fluid and fill and seal off the annular gap 156 between the piston 150 and the housing 140. In one embodiment, the seal 164 prevents any blood flow through the electrode tip 120. Alternatively, in another embodiment, the seal 164 is adapted to limit the bodily fluid which passes past the seal 164. The hydrogel seal 164 is comprised of material which expands upon contact of fluid. One suitable type of material is a hydrophilic polymer, for example poly (2-hydroxyethyl methacrylate), polyvinyl alcohol, or polyethylene oxide. Other examples include Thermedics TECOGEL, Thermedics TECOPHILLIC, and polyvinyl pyrrolidone. Alternatively, other materials which are expandable upon contact with fluid could also be used. Once expanded to fill the annular gap 156, the hydrogel seal 164 is lubricious, thereby allowing rotation of the piston 150 and the helix 100 via the stylet 14.

The hydrogel seal 164 is not limited to a retractable lead, and can be used on other medical devices such as catheters. FIGS. 3A and 3B illustrate another embodiment which includes an open lumen lead 180. The open lumen lead 180 has a lead body 182 extending to a lead tip 183, defining a lumen 184 therein. The lumen 184 is defined by an inner surface 188 of the lead body 182. The lumen 184 is used to manipulate the lead 180 over a guidewire (not shown). Since no seal is typically provided, blood and other bodily fluids can enter the lumen 184, leading to complications. A hydrogel seal 186, in one embodiment, is disposed on the inner surface 188 of the lead body 182, as shown in FIG. 3A. The hydrogel seal 186 is adapted to expand upon contact with fluid and fill and seal off the lumen 184. In one embodiment, the seal 186 prevents any further flow of blood or bodily fluid through the lead tip 183. Alternatively, in another embodiment, the seal 186 is adapted to limit the bodily fluid which passes past the seal 186. The hydrogel seal 186 is comprised of material which expands upon contact of fluid. Upon contact with fluid, the hydrogel seal 186 expands to fill the lumen 184 as shown in FIG. 3B.

Figure 4:
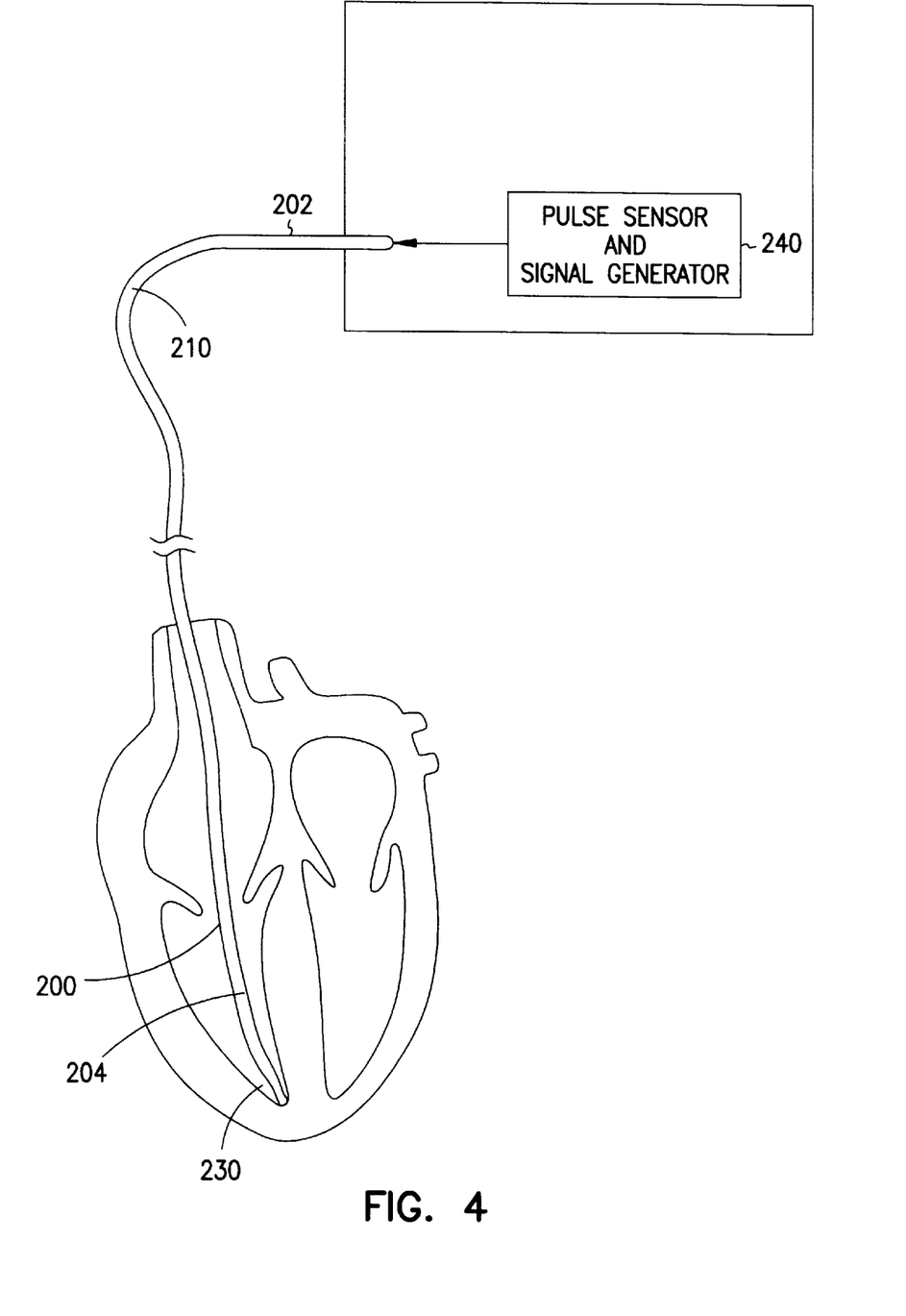
FIG. 4 is a cross-sectional view illustrating a system for delivering signals to the heart constructed in accordance with one embodiment of the present invention.

FIG. 4 illustrates another embodiment, showing a view of a lead 200 adapted for delivering electrical pulses to stimulate the heart. The lead 200 is not limited to any particular type of lead. The lead 200 extends from a proximal end 202, which is adapted to connect with equipment which supplies electrical pulses, to a distal end 204 which is adapted to be inserted into the heart. Proximate to the distal end 204 is an electrode tip 230. The electrode tip 230 includes a hydrogel seal or expandable matrix material (discussed below) disposed therein. Upon contact with fluid, as discussed above, the hydrogel seal or the expandable matrix material absorbs the fluid and expands to prevent or limit additional fluid from entering through the electrode tip 230.

A connector terminal 210 is disposed near the proximal end 202 of the lead 200. The connector terminal 210 electrically connects the various electrodes and conductors within the lead 200 to a pulse generator and signal sensor 240. The pulse sensor and generator 240 contains electronics to sense various electrical signals of the heart and also produce current pulses for delivery to the heart, depending on the type of lead 200 used. The pulse sensor and generator 240 also contains electronics and software necessary to detect certain types of arrhythmias and to correct for them. The lead terminal connector 210 provides for the electrical connection between the lead 200 and the pulse generator 240.

In another configuration, an expandable matrix can be used to seal a medical device, such as a lead tip assembly. The expandable matrix can be molded and/or machined into a plug used as an external or internal seal, as will be further discussed below. Alternatively, the expandable matrix can be used as a coating on or in a base structure, which structure can be substantially rigid. The expandable matrix is biocompatible. The expandable matrix is adapted to expand upon contact with a fluid, and is effective in sealing fluids from further entry into the medical device.

The composition of the expandable matrix, in one embodiment, generally consists of at least one water permeable polymeric material in combination with one or more osmotically active agents. One example of a water permeable polymeric material includes silicone. Other biocompatible elastomeric polymers include polyvinyl alcohol or poly (ethylene oxide), or polyurethane. The expandable matrix includes at least one osmotically active agent such as, glycerol, sodium chloride, or calcium chloride. Other equivalent agents can also be useful for forming the expandable matrix such as mannitol, glucose, dextran, potassium chloride, sodium phosphate, or any other non-toxic water soluble material that does not adversely affect curing of the water permeable polymer.

The expandable matrix is adapted to absorb water upon contact with a fluid environment. As water is absorbed, the matrix begins to swell in physical size and continues to swell until, in one embodiment, the osmotically active agent is consumed. Alternatively, in another embodiment, the expandable matrix swells until the internal pressure of the matrix is matched by a source of external pressure of, for example, the polymer or structure surrounding the polymer. The rate of expansion and/or the amount of expansion can be controlled by the selection of the polymer, the additive, and the particle size of the additive.

Other materials can be incorporated with the expandable matrix to yield additional advantages or results. For example, in one embodiment, the expandable matrix could incorporate a radiopaque material so that the matrix can be visualized using a fluoroscope. In another configuration, pharmacologic additives can be incorporated with the expandable matrix such as dexamethasone sodium phosphate, which would cause expansion of the matrix and provide local pharmacologic therapy, such as anti-inflammatory action, thus improving the biocompatibility of the device. Alternatively, additives which would promote local blood coagulation can also be incorporated, such as calcium salts, intrinsic or extrinsic clotting factors.

The amount of osmotically active agent contained within the water permeable polymeric material can be varied, depending on the desired results. For instance, the rate of expansion or the total amount of expansion can be controlled by varying the relative amounts of materials, which can be determined by testing the materials. In one embodiment, the weight content of the osmotically active agent of the expandable matrix ranges from 2%–50%. In another embodiment, the weight content of the osmotically active agent of the expandable matrix ranges from 10%–40% by weight.

Figure 5:
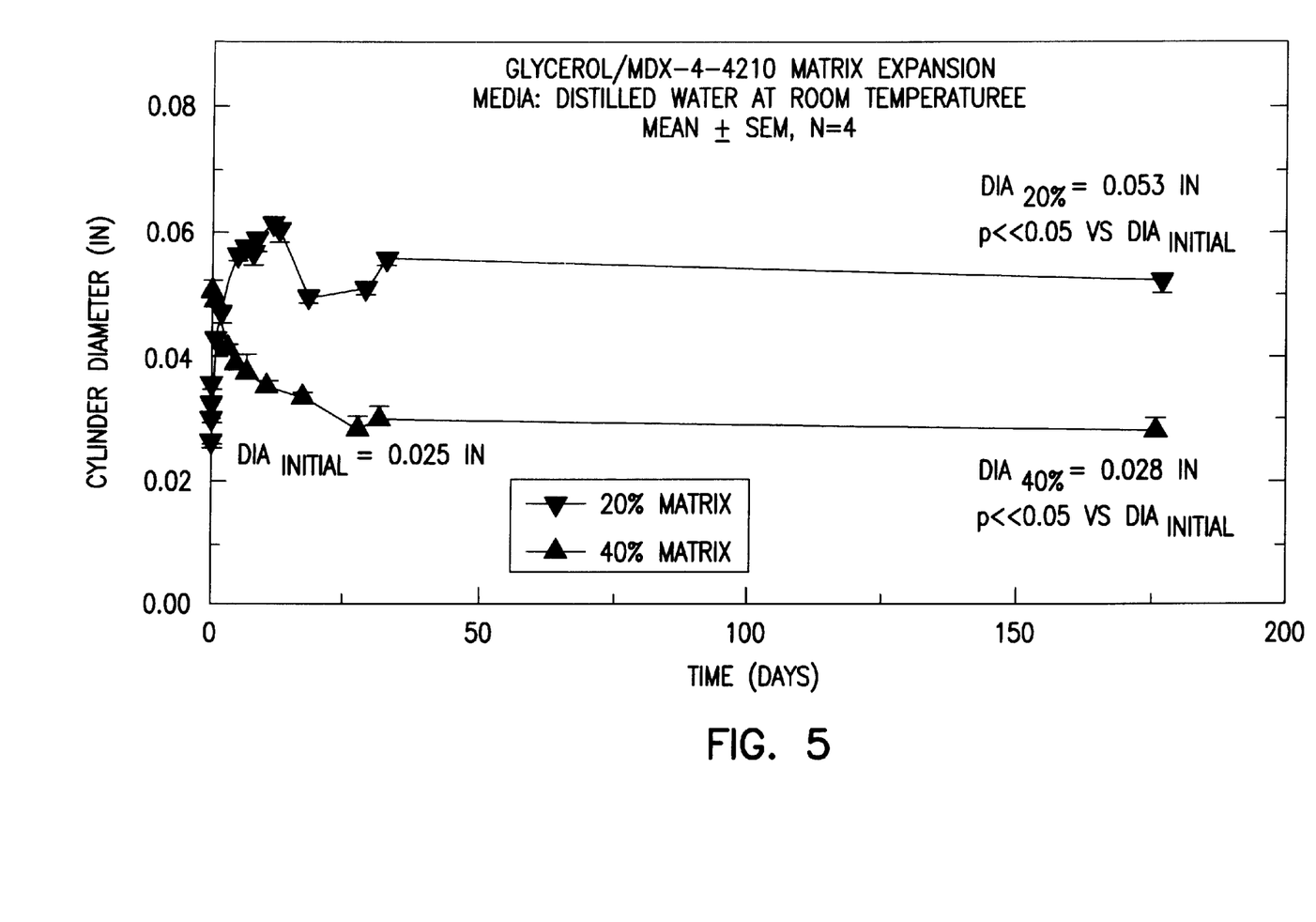
FIG. 5 is a table illustrating the expansion for the expandable matrix constructed in accordance with one embodiment of the present invention.

In one embodiment, the total amount of expansion was measured for a expandable matrix comprising water permeable polymeric material of silicone (Dow Corning MDX-4-4210) with an osmotically active agent of glycerol. The amount of glycerol, by weight percentage, was varied from 10% to 40%. The results of this testing are summarized in FIGS. 5 and 6. FIG. 5 illustrates the change in diameter of two matrix compositions over time of exposure, which shows that the fastest change in diameter occurs in the early stages of exposure. FIG. 5 also illustrates that the fastest change in diameter, i.e., the fastest rate of expansion, occurred in the early stages of the 40% glycerol/silicone matrix. However, this amount would vary for other water permeable polymeric materials and/or other osmotically active agents. These results demonstrate that the rate of expansion could be increased using increasing concentrations of glycerol. FIG. 5 also illustrates that the dimensions of the matrix containing 40% of glycerol returns to approximately the initial diameter with prolonged exposure to fluid. In contrast, the test sample containing 20% of glycerol maintains a stable, expanded dimension over the same prolonged exposure time.

Figure 6:
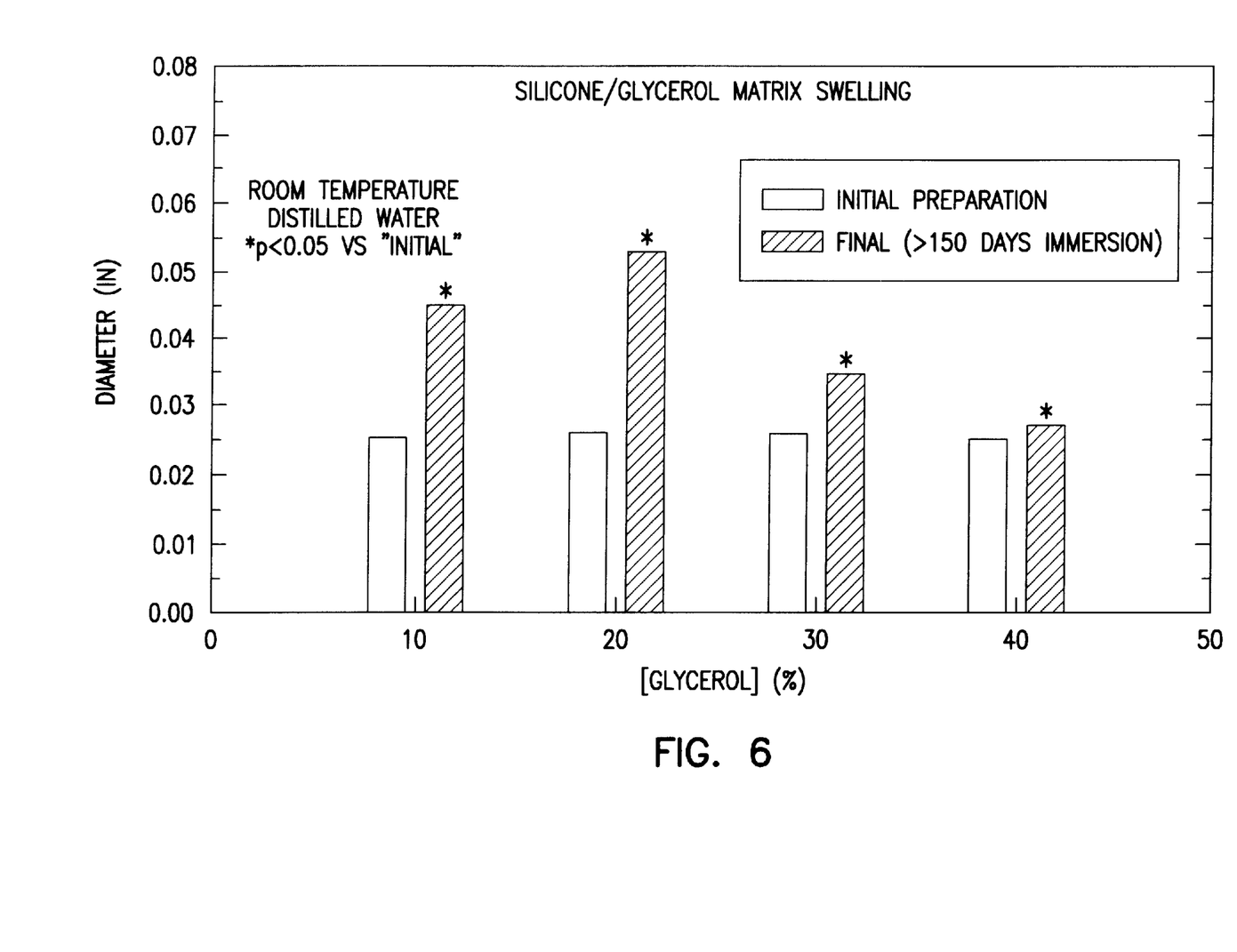
FIG. 6 is a table illustrating the amount of expansion for the expandable matrix constructed in accordance with another embodiment of the present invention.

FIG. 6 further compares final dimensions of the matrix material after prolonged exposure for compositions ranging from 10% to 40% of glycerol, measured by weight. Of the samples tested, a glycerol content of 40% yields the fastest expansion. However, a maximum stable, over time, expanded matrix size occurs with the matrix containing 20% of glycerol. Thus, the amount of glycerol content can be manipulated to modify the expansion of the expandable matrix upon initial contact with fluid as well as contact with fluid over extended periods of time.

Figure 7:
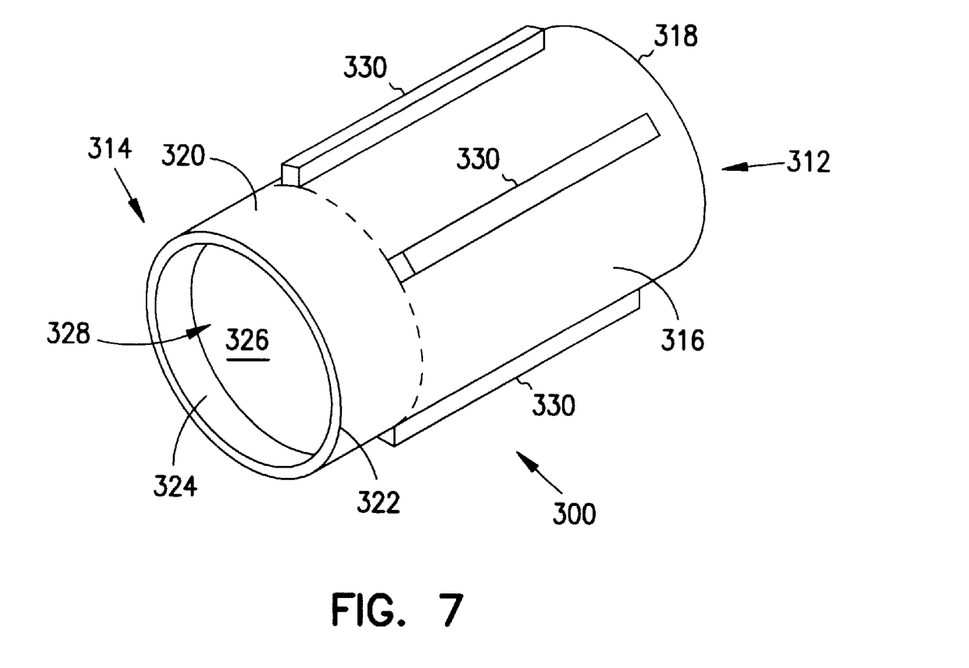
FIG. 7 is a perspective view of a plug for sealing a medical device constructed in accordance with one embodiment of the present invention.

FIG. 7 illustrates one embodiment incorporating the expandable matrix as discussed above. A plug 300 is provided which, in one embodiment, is molded from an expandable matrix which is adapted to expand upon contact with fluid. Alternatively, the plug 300 can be coated with the expandable matrix. The plug 300 extends from a first end 312 to a second end 314, and, in one embodiment, is generally cylindrically shaped. The first end 312 and the second end 314 define an intermediate portion 316 therebetween. In one embodiment, the first end 312 includes a tapered portion 318. The tapered portion 318 facilitates implantation of the plug 300 into a medical device, or movement of the plug through narrow passages.

The plug 300 is defined in part by an outer surface 320 which includes an outer diameter 322. In one embodiment, proximate the second end 314, the plug has a recess 328 therein. The recess 328 defines an inner diameter surface 324 and an advancing surface 326. The recess 328 is adapted, in one embodiment, to receive an advancing tool (FIG. 8) therein, as will be further described below. The inner diameter surface 324, in another embodiment, is adapted to frictionally engage the advancing tool therein. Alternatively, the recess 328 can be configured such that sufficient expansion of the plug 300 must occur before the advancing tool could be removed from the recess 328.

In one configuration, the outer diameter 322 of the plug 300 has at least one rib 330 disposed thereon. The at least one rib 330 can be configured in many different shapes. The at least one rib 330 is adapted to project from the outer surface 320 of the plug 300. As the plug 300 expands upon contact with fluid, the at least one rib 330 interferes with further advancement of the plug 300 through an enclosing surface and permits the plug 300 to expand to fill a lumen in which the plug 300 is disposed. As the plug 300 further expands, the at least one rib 330 is compressed by an external surface of a lumen (FIG. 8) in which the plug 300 is received. In one configuration, a plurality of ribs 332 are provided, which, in one embodiment, extend longitudinally along the plug 300. As the plurality of ribs 332 are compressed, the plug 300 is retained by the enclosing surface to allow for removal of the advancing tool 460 (FIG. 8) therefrom.

Figure 8:
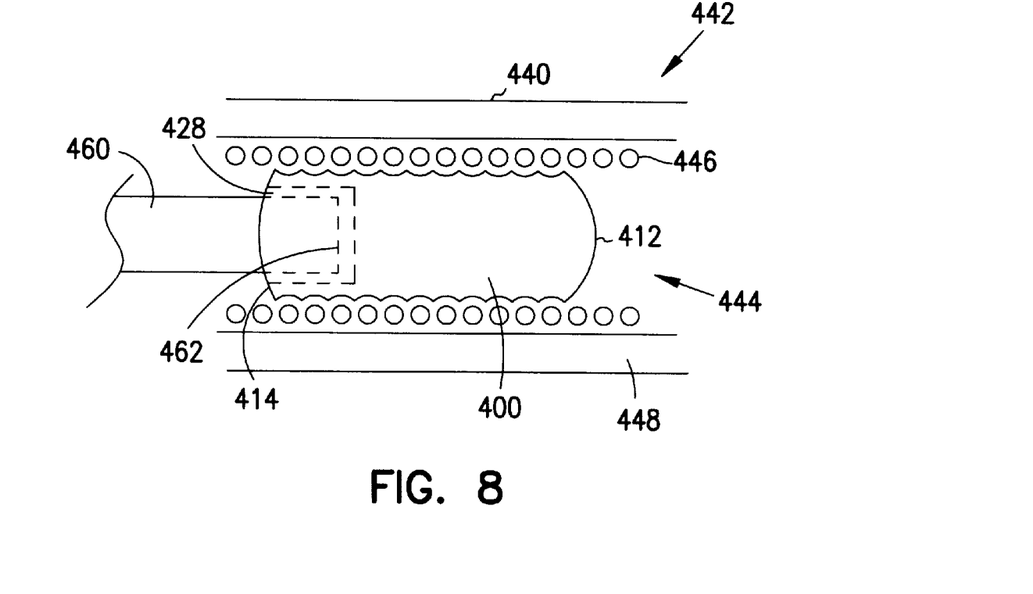
FIG. 8 is a cross-sectional view of a lead for monitoring and stimulating the heart constructed in accordance with one embodiment of the present invention.

FIG. 8 illustrates another embodiment of the present invention. In this configuration, a plug 400 is received within a medical device 440. The plug 400 is molded from an expandable matrix which is adapted to expand upon contact with fluid, as discussed above. Alternatively, the plug 400 is coated with the expandable matrix. In one embodiment, the medical device 440 comprises a lead 442 which is adapted to be implanted in or around the heart. The lead 442 comprises a number of configurations such as, although not limited to, those described above and shown in FIGS. 1–4. Disposed within the lead 442 is a coil 446, which is contained by an outer body 448, and the lead 442 has a lumen 444 therein. The plug 400 is adapted to seal the lumen 444 of the lead 442 upon expansion of the plug 400, which prevents bodily fluids from entering through the lead 442 and interfering with the performance of the lead 442.

The plug 400 extends from a first end 412 to a second end 414, and has a tapered portion, in one embodiment, proximate to the first end 412. In another configuration, the plug 400 has a recess 428 therein, which is disposed proximate the second end 414. The recess 428 is adapted to receive a distal tip 462 of an advancing tool 460 therein. Once access through the lumen 444 is no longer needed, the plug 400 can be positioned within the medical device 440. The advancing tool 460 is used to move the plug 400 through the lumen 444 of the medical device 440 and position the plug 400 in an appropriate sealing location. The plug 400 and/or the recess 428 can be modified as in the previous embodiment shown in FIG. 7 to facilitate removal of the advancing tool 460. After the plug 400 has been positioned within the medical device 440, the advancing tool 460 can be removed. Upon contact with fluid, the plug 400 will begin to expand and seal the lumen 444 of the medical device 440.

Figure 9:
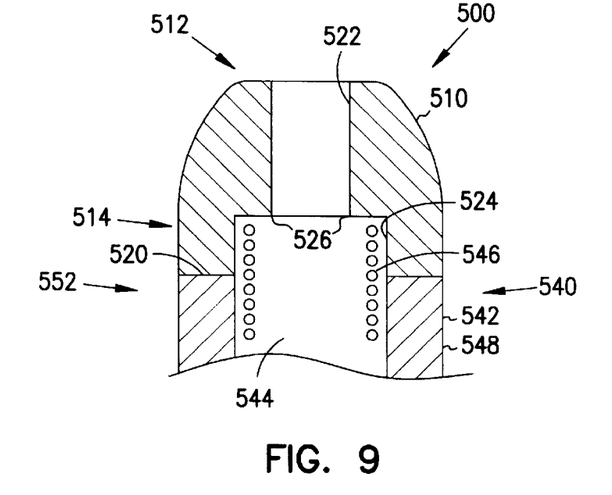
FIG. 9 is a cross-sectional view of a lead for monitoring and stimulating the heart constructed in accordance with one embodiment of the present invention.

In another configuration, as shown in FIG. 9, a plug 500 is provided which is coupled with a medical device 540. The plug 500 is molded from an expandable matrix which is adapted to expand upon contact with fluid, as discussed above. Alternatively, the plug 500 is coated with the expandable matrix. In one embodiment, the medical device 540 comprises a lead 542 which is adapted to be implanted in or around the heart. The lead 542 can comprise a number of configurations such as, although not limited to, those described above and shown in FIGS. 1–4. Disposed within the lead 542 is a coil 546, which is contained by a body having an outer diameter 548, and the lead 542 has a lumen 544 therein. The lead 542 extends to a distal end 552 where it abuts the plug 500 at an attachment surface 520. The plug 500 is adapted to seal the lumen 544 of the lead 542 upon expansion of the plug 500, which prevents bodily fluids from entering through the lead 542 and interfering with the performance of the lead 542.

The plug 500 is molded from an expandable matrix which is adapted to expand upon contact with fluid. Alternatively, the plug 500 is coated with the expandable matrix. The plug 500 extends from a first end 512 to a second end 514, and in one embodiment has an outer surface shaped as a cone 510. The plug has a first inner diameter 522 proximate the first end 512 and a second inner diameter 524 proximate the second end 514. The second inner diameter 524 is, in one embodiment, larger than the first inner diameter 522, forming a shoulder 526 therebetween.

The coil 546 of the lead 542, in one embodiment, extends past the distal end 552 of the lead 542 and is received by the second inner diameter 524 of the plug 500. The coil 546, in one embodiment, is affixed to the second inner diameter 524 such that the coil 546 rests against the shoulder 526 of the plug 500. In another configuration, the coil 546 is frictionally engaged by the surface of the second inner diameter 524. In yet another embodiment, the coil 546 can be attached to the lead 542 in a number of manners including medical adhesive.

As the plug 500 is exposed to fluids, the surface of the first inner diameter 522 begins to grow smaller and smaller until a seal is created. Once the first inner diameter 522 has been eliminated by the expansion of the expandable matrix, the lumen 544 of the medical device 540 is effectively sealed off from further entry of fluids.

Figure 10:
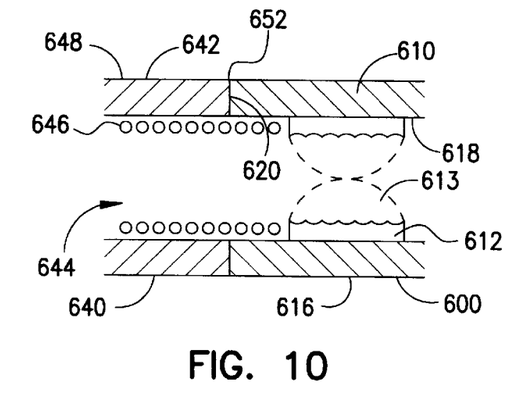
FIG. 10 is a cross-sectional view of a lead for monitoring and stimulating the heart constructed in accordance with one embodiment of the present invention.

Illustrated in FIG. 10 is another configuration, wherein a plug 600 is provided which is coupled with a medical device 640. In one embodiment, the medical device 640 comprises a lead 642 which is adapted to be implanted in or around the heart. The lead 642 can comprise a number of configurations such as, although not limited to, those described above and shown in FIGS. 1–4. Disposed within the lead 642 is a coil 646, which is contained by a lead body having an outer diameter 648, and the lead 642 has a lumen 644 therein. The lead 642 extends to a distal end 652 where it abuts the plug 600 at an attachment surface 620.

The plug 600 comprises a housing 610 having an outer diameter 616 and an inner diameter 618. The housing 610 is formed from a rigid material has expandable matrix material 612 disposed within the inner diameter 618, where the expandable matrix material 612 is adapted to expand upon contact with fluid, as discussed above. The housing 610 can be attached to the medical device 640 in a variety of manners. For instance, in one configuration, the housing 610 is laser welded to the medical device 640. Alternatively, other attachment methods can also be used, such as resistance welding or adhesive bonding. The plug 600 is adapted to seal the lumen 644 of the lead 642 upon expansion of the plug 600, which prevents bodily fluids from entering through the lead 642 and interfering with the performance of the lead 642.

The coil 646 of the lead 642, in one embodiment, extends past the distal end 652 of the lead 642 and is received by the inner diameter 618 of the plug 600. The coil 646, in one embodiment, is affixed to the inner diameter 618. The coil 646 can be affixed to the inner diameter 618 using adhesive or mechanical attachment methods. In another configuration, the coil 646 is frictionally engaged by the surface of the inner diameter 618.

As the plug 600 is exposed to fluids, the expandable matrix material 612 swells and the inner diameter 618 begins to grow smaller and smaller until a seal 613 is created. Once the inner diameter 618 has been eliminated by the expansion of the expandable matrix, the lumen 644 of the medical device 640 is effectively sealed off from further entry of fluids.

Figure 11:
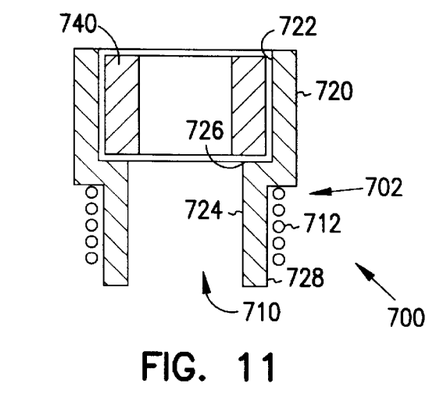
FIG. 11 is a cross-sectional view of a lead for monitoring and stimulating the heart constructed in accordance with one embodiment of the present invention.

In another configuration, as illustrated in FIG. 11, a medical device such as a lead 700 is provided which has a cup 720 affixed thereto. The cup 720 comprises, in one embodiment, a thin-walled structure which is received by the lead 700 around an outer diameter 728 of the cup 720. The cup 720 can be made from biocompatible metal alloys and/or rigid polymers. In one embodiment, the cup 720 is attached at a distal end 702 of the lead 700, for example, by welding the cup 720 to the conductor coil 712 of the lead 700. Alternatively, the cup 720 can be attached to the lead 700 in other manners.

In another embodiment, the cup 720 includes a first inner diameter 722 and a second inner diameter 724, forming a shoulder 726 therebetween. Molded expandable material 740 is provided which rests upon the shoulder 726 until expansion takes place. The molded expandable material 740 is formed from expandable matrix material, as discussed above in previous embodiments. Once the lead 700 has been implanted, and fluids contact the molded expandable material 740, the material 740 expands until it contacts the surface of the first inner diameter 722. The molded expandable material 740 can be provided in a variety of shapes to accommodate the interior surface of the cup 720. In one configuration, the expandable material 740 is provided in the shape of a ring. The ring shape allows for access to a lumen 710 of the lead 700 during implantation, yet provides an effective seal after contact with fluid.

Figure 12:
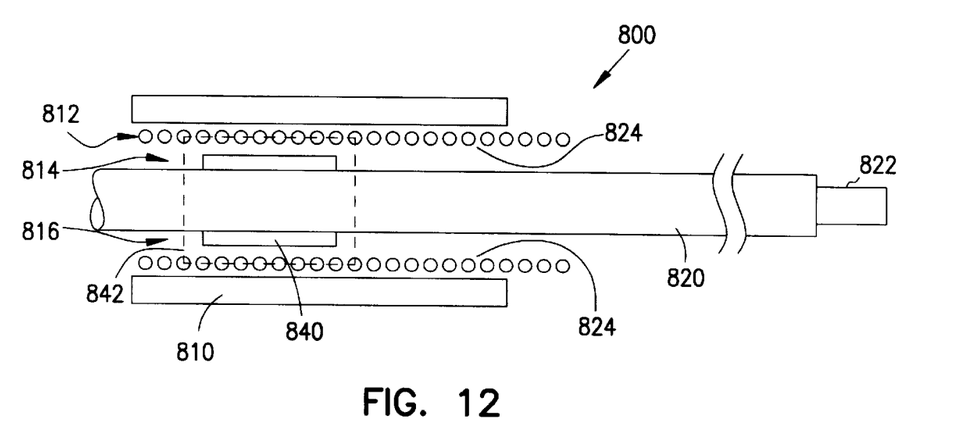
FIG. 12 is a cross-sectional view of a lead for monitoring and stimulating the heart constructed in accordance with one embodiment of the present invention.

FIG. 12 illustrates yet another configuration of a lead 800. The lead 800 has a lead body 810 containing a conductor coil 812 therein. The conductor coil 812 defines a lumen 814 within the lead 800. Disposed within the lumen 814 of the lead body 810 is a secondary, internal lead structure 820 having, in one embodiment, a distal electrode 822 and a proximal electrode 824. An annular gap 816 exists between the internal lead structure 820 and the conductor coil 812. A plug 840 (shown prior to expansion) is disposed between the internal lead structure 820 and the conductor coil 812, where the plug 840 is adapted to fill the gap 816 upon contact with fluid. In one configuration, the plug 840 is molded of the expandable matrix as discussed in the earlier embodiments. Upon contact with fluid, the plug 840 expands to the plug 842 and prevents further fluids from entering through the lumen 814 of the lead 800. The plug 840 can be provided as a resident structure of the lead 800. Alternatively, the plug 840 can be advanced through the lumen 814 using an advancing tool (FIG. 8), such as a stylet (not shown) after the internal lead structure 820 has been placed. The plug 840 advantageously seals the lumen 814, and also maintains the internal lead structure within the lumen 814. In addition, the plug 840 allows for easy maneuvering of the internal lead structure 820 during placement of the internal lead structure 820.

Figure 13:
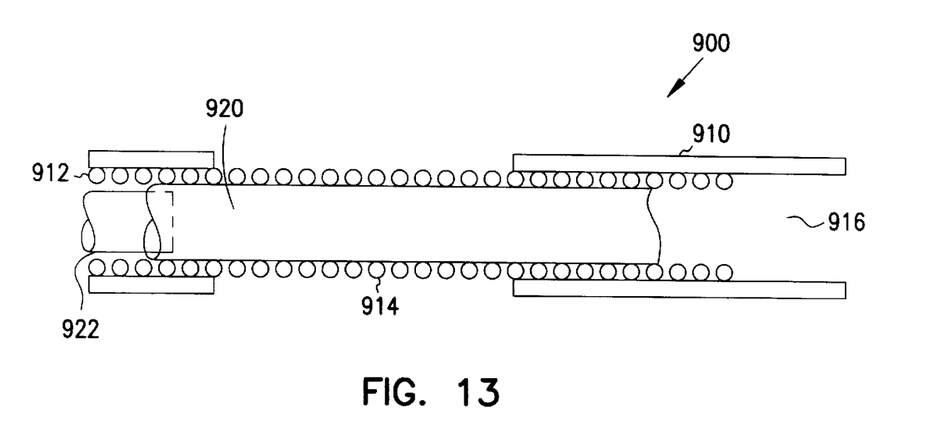
FIG. 13 is a cross-sectional view of a lead for monitoring and stimulating the heart constructed in accordance with one embodiment of the present invention.

In FIG. 13, another embodiment of a lead 900 is illustrated. The lead 900 has a lead body 910 encompassing, at least in part, a conductor coil 912. A portion of the conductor coil 912 is exposed thereby forming an exposed electrode 914. The conductor coil 912 defines a lumen 916 therein. The lumen 916, in conjunction with a guidewire, for example, can be used to position the lead 900 within the heart. However, the lumen 916 allows for entry of bodily fluids into the lead 900, which may lead to complications.

A plug 920 is provided which seals off the lumen 916 after the lead 900 is properly positioned within the heart. The plug 920 is formed from the expandable matrix material as discussed in the earlier embodiments. The plug 920, in another embodiment, could also include a steroid to reduce tissue inflammation. Upon contact with bodily fluid, the plug 920 expands and seals off the lumen 916. The plug 920 is sized and adapted to expand until it occupies enough of the lumen 916 to seal off harmful entry of fluids. The components of the expandable matrix material forming the plug 920 can be modified to provide the appropriate size plug as needed. The expanded plug 920 also provides physical support to the exposed electrode 914 so that it is not inadvertently crushed.

To seal the lumen 916, the plug 920 must be properly positioned within the lead 900. An advancing tool 922 is used, in one embodiment, to properly position the plug 920 within the lead 900. Alternatively, the plug 920 can be adapted to occupy the lead 900 as a resident structure, as discussed in the earlier embodiments. In one configuration, the advancing tool 922 has a predetermined length which allows for the tool 922 to be inserted into the lead 900 at a maximum of this predetermined length, which properly positions the plug 920 within the lumen 916. In another configuration, a limit stop, not shown, can be provided within the lumen 916 which prevents further insertion of the plug 920, and alerts the physician that proper placement of the plug has occurred.

Advantageously, the hydrogel seal and the expandable matrix allow for effective sealing of the medical device or the electrode lead upon contact with body fluid. The hydrogel seal does not significantly add to the friction when a physician or assistant rotates the stylet to rotate the piston, since the expanded hydrogel is lubricious, allowing movement of the internal components. The seal blocks or limits body fluids which attempt to enter the lumen of the electrode lead.

It is to be understood that the above description is intended to be illustrative, and not restrictive. Many other embodiments will be apparent to those of skill in the art upon reading and understanding the above description. For instance, the seal can be used with a variety of medical devices. Although the use of the lead has been described for use in a cardiac pacing system, the lead could as well be applied to other types of body stimulating systems. In addition, the lead could also be applicable to bipolar pacing leads having two separate conductors, and to multipolar pacing leads employing multiple conductor leads. The scope of the invention should, therefore, be determined with reference to the appended claims, along with the full scope of equivalents to which such claims are entitled.

what is claimed is:

1. A lead adapted for implantation on or about the heart, the lead comprising:
   an electrode tip assembly including a lumen therethrough; and
   a seal disposed within the lumen, the seal including expandable matrix material adapted to expand in volume upon contact with fluid; the seal extending from a first end to a second end, the seal having a recess therein, where said recess is adjacent to said second end.

2. The lead as recited in claim 1, wherein the expandable matrix comprises a hydrogel.

3. The lead as recited in claim 1, wherein the seal is formed from an expandable matrix comprising at least one water permeable material and one or more osmotically active agents.

4. The lead as recited in claim 3, wherein the water permeable material comprises silicone.

5. The lead as recited in claim 3, wherein the osmotically active agent comprises glycerol.

6. The lead as recited in claim 5, wherein the expandable matrix material includes approximately 2–50% of glycerol by weight.

7. The lead as recited in claim 5, wherein the expandable matrix material includes approximately 10–40% of glycerol by weight.

8. The lead as recited in claim 1, further comprising a movement mechanism at least partially disposed within the lumen and the seal is disposed on at least a part of the movement mechanism.

9. The lead as recited in claim 8, wherein the movement mechanism comprises a fixation helix disposed within the electrode tip assembly and coupled with a piston, the fixation helix comprising a conductor disposed in a helical shape.

10. The lead as recited in claim 1, wherein the expandable matrix material includes a pharmacological additive.

11. The lead as recited in claim 10, wherein the pharmacological additive comprises dexamethasone sodium phosphate.

12. The lead as recited in claim 1, further comprising:
a lead body having a first end and a second end;
an electrode disposed proximate the first end of the lead body;
a connector terminal disposed at the second end of the lead body, the connector terminal for connecting with a pulse generating unit;
the electrode tip assembly disposed proximate one end of the electrode;
a helix disposed within the electrode tip assembly, the helix comprising a conductor disposed in a helical shape, wherein the helix rotates around an axis of the electrode thereby placing the helix in extension and retraction;
a piston operatively coupled with the helix; and
the seal disposed on at least a portion of the piston.

13. A system for delivering signals to the heart, the system comprising:
an electronics system including a cardiac activity sensor and a signal generator for producing signals to stimulate the heart; and
a lead adapted for implantation on or about the heart and operatively coupled with the electronics system, the lead comprising:
an electrode tip assembly having a lumen therethrough; and
a seal disposed within the lumen, the seal being comprised of expandable matrix material being adapted to expand in volume upon contact with fluid, the seal having a first end surface positioned to couple with a removable advancing tool for positioning the seal within the lumen.

14. The system as recited in claim 13, the electrode tip assembly further comprising a helix disposed within the electrode tip assembly, the helix comprising a conductor disposed in a helical shape, wherein the helix rotates around an axis of the electrode tip assembly.

15. The system as recited in claim 13, wherein the expandable matrix material comprises a hydrogel.

16. The system as recited in claim 13, the seal further comprising radiopaque material.

17. The system as recited in claim 13, wherein the expandable matrix material includes a pharmacological additive.

18. The system as recited in claim 13, wherein the expandable matrix comprises at least one water permeable material and one or more osmotically active agents.

19. The system as recited in claim 18, wherein the water permeable material comprises silicone.

20. The system as recited in claim 18, wherein the osmotically active agent comprises glycerol.

21. A lead adapted for implantation on or about the heart, the lead comprising:
an electrode tip having a lumen therethrough; and
a lumen plug disposed within the lumen, the lumen plug adapted to expand in volume upon contact with fluid, said lumen plug having a receptacle portion which is sized to receive a removable advancing tool therein for positioning the lumen plug within the lumen.

22. The lead as recited in claim 21, wherein the plug extends from a first portion of the plug to a second portion of the plug, the first portion of the plug having a tapered shape.

23. The lead as recited in claim 22, wherein the second portion includes a recess therein.

24. The lead as recited in claim 22, further comprising at least one rib disposed between the first portion and the second portion.

25. The lead as recited in claim 24, wherein the rib is adapted to release an advancing tool from the second end upon expansion of the plug.

26. The lead as recited in claim 24, wherein a plurality of ribs extend longitudinally along the plug.

27. The lead as recited in claim 24, wherein the plug is coated with expandable matrix material.

28. The lead as recited in claim 24, wherein at least a portion of the plug is formed from expandable matrix material.

29. The lead as recited in claim 28, wherein the expandable matrix material includes a pharmacological additive.

30. A lead adapted for implantation on or about the heart, the lead comprising:
an electrode tip having a lumen therethrough;
a lumen plug disposed within the lumen, the lumen plug adapted to expand in volume upon contact with fluid, the plug extending from a first portion of the plug to a second portion of the plug, the first portion of the plug having a tapered shape; and
the second portion of the plug comprising a receptacle end sized to receive a removable advancing tool therein.

31. The lead as recited in claim 1, wherein the recess is adapted to frictionally engage an advancing tool.

32. The lead as recited in claim 1, wherein the first end has a tapered portion.

33. A lead comprising:
a lead body having a first end and a second end;
a conductor disposed within the lead body, the lead body encompassing only a portion of the conductor forming an exposed conductor portion, the exposed conductor portion comprising an exposed electrode;
the conductor having a lumen therein; and
a seal disposed within the lumen, the seal including expandable matrix material adapted to expand in volume upon contact with fluid, the seal having a surface which couples with a removable advancing tool for positioning the seal within the lumen.

34. The lead as recited in claim 33, wherein the seal is disposed adjacent to the exposed electrode.

35. The lead as recited in claim 33, wherein the seal extends from a first end to a second end, the second end adapted to frictionally engage an advancing tool.

36. The lead as recited in claim 33, wherein the seal extends from a first end to a second end, the first end having a tapered portion.

37. A lead adapted for implantation on or about the heart, the lead comprising:

an electrode tip having a lumen therethrough; and a lumen plug disposed within the lumen, the lumen plug adapted to expand in volume upon contact with fluid, said lumen plug adapted to receive an advancing tool therein;

wherein the plug extends from a first portion of the plug to a second portion of the plug, the first portion of the plug having a tapered shape, the second portion of the plug includes a recess therein.

* * * * *